(12) United States Patent
Ellis

(10) Patent No.: US 11,235,110 B1
(45) Date of Patent: Feb. 1, 2022

(54) DELIVERY SYSTEM FOR AYAHUASCA-LIKE SUBSTANCES

(71) Applicant: Gregory Ellis, Portland, OR (US)

(72) Inventor: Gregory Ellis, Portland, OR (US)

(*) Notice: Subject to any disclaimer, the term of this patent is extended or adjusted under 35 U.S.C. 154(b) by 0 days.

(21) Appl. No.: 17/394,340

(22) Filed: Aug. 4, 2021

Related U.S. Application Data

(63) Continuation of application No. PCT/US2021/042123, filed on Jul. 18, 2021.

(60) Provisional application No. 63/144,923, filed on Feb. 2, 2021, provisional application No. 63/058,444, filed on Jul. 29, 2020.

(51) Int. Cl.
| | | |
|---|---|---|
| *A61M 11/00* | (2006.01) | |
| *A61K 31/40* | (2006.01) | |
| *A61M 11/04* | (2006.01) | |
| *A61K 31/4045* | (2006.01) | |
| *A61K 47/10* | (2017.01) | |

(52) U.S. Cl.
CPC ....... *A61M 11/042* (2014.02); *A61K 31/4045* (2013.01); *A61K 47/10* (2013.01); *A61M 2205/8206* (2013.01); *C07B 2200/05* (2013.01)

(58) Field of Classification Search
CPC .............................. A61M 11/00; A61K 31/40
USPC ...................... 128/200.14; 514/415
See application file for complete search history.

(56) References Cited

U.S. PATENT DOCUMENTS

| | | |
|---|---|---|
| 2016/0081395 A1 | 3/2016 | Thorens et al. |
| 2016/0120220 A1 | 5/2016 | Malgat et al. |
| 2017/0095624 A1 | 4/2017 | Davidson et al. |
| 2017/0106153 A1 | 4/2017 | Davidson et al. |
| 2017/0119979 A1 | 5/2017 | Davidson et al. |
| 2017/0119981 A1 | 5/2017 | Davidson et al. |
| 2017/0127727 A1 | 5/2017 | Davidson et al. |
| 2017/0157343 A1 | 6/2017 | Davidson et al. |
| 2017/0203058 A1 | 7/2017 | Davidson et al. |
| 2018/0042304 A1 | 2/2018 | Hogwood et al. |
| 2018/0042305 A1 | 2/2018 | Hogwood et al. |
| 2018/0070647 A1 | 4/2018 | Labs |
| 2018/0104425 A1 | 4/2018 | Hogwood et al. |
| 2018/0289905 A1 | 10/2018 | Hogwood et al. |
| 2018/0318529 A1 | 11/2018 | Davidson et al. |
| 2019/0001087 A1 | 1/2019 | Davidson et al. |
| 2019/0009039 A1 | 1/2019 | Davidson et al. |
| 2019/0290862 A1 | 9/2019 | Davidson et al. |
| 2020/0178616 A1 | 6/2020 | Yu |
| 2020/0360239 A1 | 11/2020 | Campos |

FOREIGN PATENT DOCUMENTS

| | | |
|---|---|---|
| WO | WO2016001926 | 1/2016 |
| WO | WO2017122196 | 7/2017 |

OTHER PUBLICATIONS

Black, Lester, New on the Black Market: Vape Pens Full of DMT, The Stranger, Aug. 15, 2018. United States.
Vapor Vanity Staff, DMT Vape Pens: What You Need to Know, Vapor Vanity, May 12, 2019.
Palhano-Fontes, Fernanda et al, Rapid antidepressant effects of the psychedelic ayahuasca in treatment-resistant depression: a randomized placebo-controlled trial, Psychological Medicine 49, 655-, Apr. 24, 2018, https://doi.org/10.1017/S0033291718001356.
PCT Search Report for International application No. PCT/US2021/042123.

*Primary Examiner* — Raymond J Henley, III

(57) ABSTRACT

Provided herein is a delivery device and vaporizable formulations that provide users or patients with the ability to safely, reliably, and conveniently obtain a high-quality, therapeutic vapor comprising an ayahuasca-like substance. The delivery device includes a chamber coupled to a power unit capable of providing power to vaporize the formulations for consumption of the substance in a consistently desirable and safe manner. Further included are kits and methods of treating psychological disorders using the delivery device and vaporizable formulations provided herein.

20 Claims, 4 Drawing Sheets

DELIVERY SYSTEM FOR AYAHUASCA-LIKE SUBSTANCES

CROSS-REFERENCE TO RELATED APPLICATIONS

This application is a continuation under 35 USC 365(c) of International Application No. PCT/US21/42123, filed Jul. 18, 2021, which claims priority benefit to U.S. Provisional Application No. 63/058,444, filed Jul. 29, 2020, and U.S. Provisional Application No. 63/144,923, filed Feb. 2, 2021, the entire contents of each of which are hereby incorporated by reference.

BACKGROUND OF THE INVENTION

In certain jurisdictions, ayahuasca-like substances and other psychedelic medicines are being legalized or decriminalized, hence allowing for breakthrough alternative medicines and/or recreational experiences. Psychedelic research is still in its infancy, which in part is a consequence of legal barriers to such research that has existed for decades. Yet preliminary reports are encouraging. For example, it was recently reported that dimethyltryptamine, which is the active ingredient in ayahuasca, can promote the proliferation of neural stem cells and subsequent neurogenesis, thus leading to improvements in memory. Such results have significant implications for neurodegenerative disorders such as Alzheimer's, Parkinson's, and dementia (Morales-Garcia et al., *Translational Psychiatry*, 10:331 (2020)).

However, the ability to distribute reliably consistent amounts and types of ayahuasca-like substances having a particular level of therapeutic or recreational quality is limited. Safety concerns may also arise when ayahuasca-like substances are obtained in a manner where the exact composition is unknown due to risks of contamination, tampering, misrepresentation, etc.

The ability to store and seal a dose-specific vaporizable formulation comprising an ayahuasca-like substance in a controlled environment with a labelled package that is easily portable provides a tremendous benefit to patients and other consumers. When an ayahuasca-like substance comes preprocessed and stored in a dry, secure, contamination-free environment, a patient or other consumer is provided with a level of confidence and convenience that has not previously been available. The devices and methods of the present invention thus solve problems associated with both ease of use and safety, and further provide a greater degree of legitimacy so that a patient or consumer can be confident that the contents of the packaged product is in fact what is listed by the labelling.

The invention described herein provides a device, formulation, methods of use, methods of treatment of psychological disorders, and kits for the delivery of ayahuasca-like substances, which has significant commercial and medicinal potential in jurisdictions that have legalized or decriminalized psychedelic substances.

SUMMARY OF THE INVENTION

The present teachings relate to a system for the delivery of a vaporizable formulation comprising an ayahuasca-like substance.

In an embodiment, a device for the delivery of an ayahuasca-like substance is provided. The device comprises a chamber comprising at least one vaporizable formulation wherein the vaporizable formulation comprises the ayahuasca-like substance. In an embodiment, the chamber of the device comprises a top portion adapted for coupling to a mouthpiece wherein the top portion of the chamber comprises at least one aperture adapted to permit flow of air, liquid, solids, or vapor between the top portion of the chamber and the mouthpiece. In an embodiment, a mouthpiece of the device coupled to the top portion of the chamber is provided wherein the mouthpiece comprises a top aperture, a central open bore, a bottom portion comprising an aperture, and wherein the bottom portion of the mouthpiece is coupled to the top portion of the chamber. In an embodiment, at least one seal situated between the bottom portion of the mouthpiece of the device comprising an aperture and the top portion of the chamber is provided. In an embodiment, the mouthpiece of the device is releasably coupled to the top portion of the chamber. In an embodiment, the mouthpiece of the device is lockably coupled to the top portion of the chamber. In an embodiment, the chamber of the device comprises a bottom portion adapted for coupling to a power unit capable of providing power to vaporize the vaporizable formulation. In an embodiment, the chamber of the device is coupled to the power unit capable of providing power to vaporize the vaporizable formulation. In an embodiment, the chamber of the device is releasably coupled to the power unit. In an embodiment, the chamber of the device is lockably coupled to the power unit. In an embodiment, the chamber of the device comprises one or more of a 401, 510, 601, 610, 710, 808, 901, 4081, CE-4, CE-5, E9, or eGo connector. In an embodiment, the chamber of the device comprises a 510 connector. In an embodiment, the chamber of the device is transparent to permit visualization of levels of the vaporizable formulation. In an embodiment, the chamber of the device is refillable. In an embodiment, the ayahuasca-like substance or vaporizable formulation of the device comprises one or more of dimethyltryptamine, a monoamine oxidase inhibitor, 5-methoxy-N,N-dimethyltryptamine, or 2-5-dimethoxy-4-bromophenethylamine. In an embodiment, the ayahuasca-like substance of the device comprises dimethyltryptamine. In an embodiment, the ayahuasca-like substance of the device comprises an isotopomer or isotopologue of one or more of dimethyltryptamine, a monoamine oxidase inhibitor, 5-methoxy-N,N-dimethyltryptamine, or 2-5-dimethoxy-4-bromophenethylamine. In an embodiment, the ayahuasca-like substance of the device is dimethyltryptamine comprising deuterium. In an embodiment, the vaporizable formulation of the device comprises one or more of propylene glycol (PG), vegetable glycerin (VG), or polyethylene glycol (PEG).

In another embodiment, a method for delivering an ayahuasca-like substance is provided. In this embodiment the method comprises heating a vaporizable formulation comprising the ayahuasca-like substance to vaporize at least a portion of the vaporizable formulation. In an embodiment, the vaporizable formulation of the method is housed in a chamber comprising a top portion adapted for coupling to a mouthpiece wherein the top portion of the chamber comprises at least one aperture adapted to permit flow of air, liquid, solids, or vapor between the top portion of the chamber and the mouthpiece. In an embodiment, the chamber of the method comprises a mouthpiece coupled to the top portion of the chamber wherein the mouthpiece comprises a top aperture, a central open bore, a bottom portion comprising an aperture, and wherein the bottom portion of the mouthpiece is coupled to the top portion of the chamber. In an embodiment, the chamber of the method comprises at least one seal situated between the bottom portion of the mouthpiece comprising an aperture and the top portion of the chamber. In an embodiment, the mouthpiece of the method is releasably coupled to the top portion of the chamber. In an embodiment, the mouthpiece of the method is lockably coupled to the top portion of the chamber. In an embodiment, the chamber of the method comprises a bottom portion adapted for coupling to a power unit capable of providing power to vaporize the vaporizable formulation. In an embodiment, the chamber of the method is coupled to the power unit capable of providing power to vaporize the vaporizable formulation. In an embodiment, the chamber of the method is releasably coupled to the power unit. In an embodiment, the chamber of the method is lockably coupled to the power unit. In an embodiment, the chamber of the method comprises one or more of a 401, 510, 601, 610, 710, 808, 901, 4081, CE-4, CE-5, E9, or eGo connector. In an embodiment, the chamber of the method comprises an eGo connector. In an embodiment, the chamber of the method comprises a 510 connector. In an embodiment, the chamber of the method is refillable. In an embodiment, the chamber of the method is single-use. In an embodiment, the chamber of the method is transparent to permit visualization of levels of the vaporizable formulation. In an embodiment, the ayahuasca-like substance or vaporizable formulation of the method comprises one or more of dimethyltryptamine, a monoamine oxidase inhibitor, 5-methoxy-N,N-dimethyltryptamine, or 2-5-dimethoxy-4-bromophenethylamine. In an embodiment, the ayahuasca-like substance of the method comprises dimethyltryptamine. In an embodiment, the ayahuasca-like substance of the method comprises an isotopomer or isotopologue of one or more of dimethyltryptamine, a monoamine oxidase inhibitor, 5-methoxy-N,N-dimethyltryptamine, or 2-5-dimethoxy-4-bromophenethylamine. In an embodiment, the ayahuasca-like substance of the method is dimethyltryptamine comprising deuterium. In an embodiment, the vaporizable formulation of the method comprises one or more of propylene glycol (PG), vegetable glycerin (VG), or polyethylene glycol (PEG).

In another embodiment, a vaporizable formulation is provided. In this embodiment the vaporizable formulation comprises an ayahuasca-like substance. In an embodiment, the ayahuasca-like substance or vaporizable formulation comprises one or more of dimethyltryptamine, a monoamine oxidase inhibitor, 5-methoxy-N,N-dimethyltryptamine, or 2-5-dimethoxy-4-bromophenethylamine. In an embodiment, the ayahuasca-like substance of the vaporizable formulation comprises dimethyltryptamine. In an embodiment, the ayahuasca-like substance of the vaporizable formulation comprises an isotopomer or isotopologue of one or more of dimethyltryptamine, a monoamine oxidase inhibitor, 5-methoxy-N,N-dimethyltryptamine, or 2-5-dimethoxy-4-bromophenethylamine. In an embodiment, the ayahuasca-like substance of the vaporizable formulation is dimethyltryptamine comprising deuterium. In an embodiment, the vaporizable formulation comprises one or more of propylene glycol (PG), vegetable glycerin (VG), or polyethylene glycol (PEG).

In another embodiment, a method of treating a psychological disorder is provided. In this embodiment the method comprises administering to a patient an effective amount of an ayahuasca-like substance, wherein the method comprises heating a vaporizable formulation comprising the ayahuasca-like substance to vaporize at least a portion of the vaporizable formulation. In an embodiment, the vaporizable formulation of the method of treatment is housed in a chamber comprising a top portion adapted for coupling to a mouthpiece wherein the top portion of the chamber comprises at least one aperture adapted to permit flow of air, liquid, solids, or vapor between the top portion of the chamber and the mouthpiece. In an embodiment, the chamber of the method of treatment comprises a mouthpiece coupled to the top portion of the chamber wherein the mouthpiece comprises a top aperture, a central open bore, a bottom portion comprising an aperture, and wherein the bottom portion of the mouthpiece is coupled to the top portion of the chamber. In an embodiment, the chamber of the method of treatment comprises at least one seal situated between the bottom portion of the mouthpiece comprising an aperture and the top portion of the chamber. In an embodiment, the mouthpiece of the method of treatment is releasably coupled to the top portion of the chamber. In an embodiment, the mouthpiece of the method of treatment is lockably coupled to the top portion of the chamber. In an embodiment, the chamber of the method of treatment comprises a bottom portion adapted for coupling to a power unit capable of providing power to vaporize the vaporizable formulation. In an embodiment, the chamber of the method of treatment is coupled to the power unit capable of providing power to vaporize the vaporizable formulation. In an embodiment, the chamber of the method of treatment is releasably coupled to the power unit. In an embodiment, the chamber of the method of treatment is lockably coupled to the power unit. In an embodiment, the chamber of the method of treatment comprises one or more of a 401, 510, 601, 610, 710, 808, 901, 4081, CE-4, CE-5, E9, or eGo connector. In an embodiment, the chamber of the method of treatment comprises an eGo connector. In an embodiment, the chamber of the method of treatment comprises a 510 connector. In an embodiment, the chamber of the method of treatment is refillable. In an embodiment, the chamber of the method of treatment is single-use. In an embodiment, the chamber of the method of treatment is transparent to permit visualization of levels of the vaporizable formulation. In an embodiment, the ayahuasca-like substance or vaporizable formulation of the method of treatment comprises one or more of dimethyltryptamine, a monoamine oxidase inhibitor, 5-methoxy-N,N-dimethyltryptamine, or 2-5-dimethoxy-4-bromophenethylamine. In an embodiment, the ayahuasca-like substance of the method of treatment comprises dimethyltryptamine. In an embodiment, the ayahuasca-like substance of the method of treatment comprises an isotopomer or isotopologue of one or more of dimethyltryptamine, a monoamine oxidase inhibitor, 5-methoxy-N,N-dimethyltryptamine, or 2-5-dimethoxy-4-bromophenethylamine. In an embodiment, the ayahuasca-like substance of the method of treatment is dimethyltryptamine comprising deuterium. In an embodiment, the vaporizable formulation of the method of treatment comprises one or more of propylene glycol (PG), vegetable glycerin (VG), or polyethylene glycol (PEG). In an embodiment, the psychological disorder of the method of treatment comprises one or more of obsessive compulsive disorder, nicotine addiction, alcoholism, narcotic addiction, depression and anxiety related to diagnosis of a life-threatening or terminal illness, major depressive disorder, depression, bipolar disorder, dysthymic disorder, panic attacks, schizophrenia, attention deficit disorder, attention deficit hyperactivity disorder, general anxiety disorder, impulse disorders, delusional disorders, cluster headaches, migraines, personality disorders, gambling disorders, eating disorder, body dysmorphic disorder, or post traumatic stress disorder.

In another embodiment, a kit is provided. The kit comprises a chamber comprising at least one vaporizable formulation wherein the vaporizable formulation comprises an ayahuasca-like substance. In an embodiment, the chamber of the kit comprises a mouthpiece coupled to the top portion of the chamber wherein the mouthpiece comprises a top aperture, a central open bore, a bottom portion comprising an aperture, and wherein the bottom portion of the mouthpiece is coupled to the top portion of the chamber. In an embodiment, the mouthpiece of the kit is releasably coupled to the top portion of the chamber. In an embodiment, the mouthpiece of the kit is lockably coupled to the top portion of the chamber. In an embodiment, the chamber of the kit is coupled to the power unit capable of providing power to vaporize the vaporizable formulation. In an embodiment, the chamber of the kit is releasably coupled to the power unit. In an embodiment, the chamber of the kit is lockably coupled to the power unit. In an embodiment, the chamber of the kit comprises one or more of a 401, 510, 601, 610, 710, 808, 901, 4081, CE-4, CE-5, E9, or eGo connector. In an embodiment, the chamber of the kit comprises a 510 connector. In an embodiment, the chamber of the kit is transparent to permit visualization of levels of the vaporizable formulation. In an embodiment, the chamber of the kit is refillable. In an embodiment, the ayahuasca-like substance or vaporizable formulation of the kit comprises one or more of dimethyltryptamine, a monoamine oxidase inhibitor, 5-methoxy-N,N-dimethyltryptamine, or 2-5-dimethoxy-4-bromophenethylamine. In an embodiment, the ayahuasca-like substance of the kit comprises dimethyltryptamine. In an embodiment, the ayahuasca-like substance of the kit comprises an isotopomer or isotopologue of one or more of dimethyltryptamine, a monoamine oxidase inhibitor, 5-methoxy-N,N-dimethyltryptamine, or 2-5-dimethoxy-4-bromophenethylamine. In an embodiment, the ayahuasca-like substance of the kit is dimethyltryptamine comprising deuterium. In an embodiment, the vaporizable formulation of the kit comprises one or more of propylene glycol (PG), vegetable glycerin (VG), or polyethylene glycol (PEG).

BRIEF DESCRIPTION OF THE DRAWINGS

A skilled artisan will understand that the drawings, described below, are for illustrative purposes only. The drawings are not intended to limit the scope of the present teachings in any way.

DETAILED DESCRIPTION OF THE INVENTION

Figure 1:
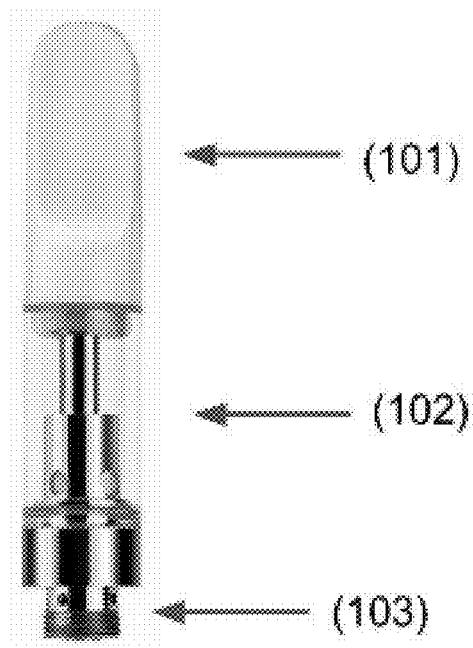
FIG. 1 illustrates an exemplary chamber of the present invention. The chamber comprises a mouthpiece (101) coupled to the top portion of the chamber, a transparent wall (102) to permit visualization of a vaporizable formulation that may be present within the hollow section of the chamber, and a threaded 510 connector (103).

The present teachings relate generally to a delivery device that provides users with the ability to safely, reliably, and conveniently obtain a high-quality, therapeutic, and vaporizable formulation comprising an ayahuasca-like substance, such as dimethyltryptamine.

Devices used to vaporize substances are known in the art, and are commonly referred to in the art as vaporizers, atomizers (e.g., rebuildable atomizers, rebuildable dripping atomizers, rebuildable tank atomizers, clearomizers, or cartomizers), mods (including but not limited to squonk mods, sub ohm mods, box mods, tube modes, temperature control mods, regulated mods, and mechanical mods), E-cigs, vape pens, etc.

During use, power may be generated by a power unit through the application of voltage generated by the power unit, which is then passed through to threads of a chamber, thus permitting a heating element that may be positioned within the chamber to generate heat. The heat may then vaporize a vaporizable formulation in the chamber adjacent to the heating element present in the chamber. The vaporizable formulation comprising the ayahuasca-like substance may then be inhaled by the user of the chamber. These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The terminology used in the disclosure herein is for the purpose of describing particular embodiments only and is not intended to be limiting of the disclosure. As used in the description of the embodiments of the disclosure and the appended claims, the singular forms of "a," "an," and "the" are intended to include the plural forms as well, unless the context clearly indicates otherwise. Also, as used herein, "and/or" refers to and encompasses any and all possible combinations of one or more of the associated listed ites. Furthermore, the term "about," as used herein when referring to a measurable value such as an amount of a compound, amount, dose, time, temperature of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this disclosure belongs.

Definitions

As used herein, an "aperture" refers to an opening, e.g. within a mouthpiece, chamber, or power unit, that permits the flow of air, liquids, solids, or vapor between components of the invention as described herein.

As used herein, an "ayahuasca-like substance" refers to an substance having any amount or sort of psychological or psychedelic effect, which can include, but is not limited to, dimethyltryptamine (also known as N,N-dimethyltryptamine, or DMT), a monoamine oxidase inhibitor, 5-methoxy-N,N-dimethyltryptamine, or 2-5-dimethoxy-4-bromophenethylamine. Ayahuasca-like substances may include isotopomer or isotopologue variations thereof, including but not limited to deuterium-containing substances. In some embodiments the ayahuasca-like substance is dimethyltryptamine. The ayahuasca-like substances of the present invention can be mixed with additional substances in the vaporizable formulation, e.g., monoamine oxidase inhibitors.

As used herein, a "chamber" refers to a device that holds a vaporizable formulation comprising an ayahuasca-like substance. A chamber is analogous to a "vape cartridge" well known in the art that may include a top portion connected to a mouthpiece, and a bottom portion connected to a battery or power supply that provides power to a heating element that may be present in the chamber that functions to heat the vaporizable formulation to produce vapor.

As used herein, a "connector" or "connection" refers to the type of connection between the chamber and the power unit. A connector may include a tenon (or "male" component) to connect the chamber to a mortise (or "female" component) configured within the power unit. In most embodiments the chamber will have the tenon and the power unit will have the mortise. The type of connectors described herein are usually referred to by the thread type, which can include, but is not limited to, 401, 510, 601, 610, 710, 808, 901, 4081, CE-4, CE-5, E9, or eGo thread. By way of example, a "510 connector" is a connector having a 510 thread as is commonly referred to in the art. In preferred embodiments a "510 connector" means the chamber is adapted with a 510 threaded tenon and the power unit has a 510 mortise able to accept a 510 threaded tenon, as is commonly referred to in the art. An eGo thread can have any diameter, but in most cases as used herein refers to an approximately 14 mm diameter. An eGo thread is usually larger than other threads used in the art, such that a smaller thread, e.g., a 510 thread, can be adapted to function with an eGo connector.

As used here, "delivery" or "delivering" refers to the delivery of an ayahuasca-like substance present within a vaporizable formulation-produced vapor generated by power supplied to the chamber of the present invention.

As used herein, "lockably coupled" refers to components that are not intended to be removed by an end-using consumer. For illustrative purposes, a mouthpiece that is lockably coupled to a chamber is not intended to be removed. Lockably coupled chambers are intended for single-use and are meant to be discarded following vaporization of all the vaporizable formulation present in a chamber. As used herein, "releasably coupled" refers to components that may be removed by an end-using consumer. For illustrative purposes, a mouthpiece that is releasably coupled to a chamber may be removed so that a user may reuse and refill a chamber with additional vaporizable formulation.

As used herein, "monoamine oxidase inhibitor" or "MAO inhibitor" refers to a compound that acts by inhibiting the activity of monoamine oxidase.

As used herein, a "mouthpiece" refers to a component that permits a user to easily inhale vapor produced within the chamber. Mouthpieces may be many different sizes and shapes, for example, flat, round, oval, square, rectangular, etc. The mouthpiece may be made of any suitable material, including but not limited to, plastic, glass, ceramic, silicon, or wood.

As used herein, the terms "propylene glycol (PG)," "vegetable glycerin (VG)," and "polyethylene glycol (PEG)" refer to components of vaporizable formulations that are substances commonly used as food additives, and have other medical applications, and which are commonly used substances known in the field of vaporizing. The components can be an molecular weight variation, for example but not limited to, PEG 200, PEG 400, and the like.

As used herein, "refillable" refers to a chamber that may be refilled and reused. This is opposed to a "single-use" chamber, which is not meant to be refillable.

As used herein, "power" refers to energy capable of generating heat within a heating element capable of producing vapor as described herein.

As used herein, a "power unit" refers to a device meant to provide power, e.g., voltage, to vaporize a vaporizable formulation comprising an ayahuasca-like substance within the chamber of the present invention.

As used herein, a "psychological disorder" refers to any disorder that may be treated by the methods and devices of the present invention. Non-limiting examples of psychological disorders may include, but are not limited to, obsessive compulsive disorder, nicotine addiction, alcoholism, narcotic addiction, depression and anxiety related to diagnosis of a life-threatening or terminal illness, major depressive disorder, depression, bipolar disorder, dysthymic disorder, panic attacks, schizophrenia, attention deficit disorder, attention deficit hyperactivity disorder, general anxiety disorder, impulse disorders, delusional disorders, cluster headaches, personality disorders, gambling disorders, eating disorder, body dysmorphic disorder, or post traumatic stress disorder.

As used herein, a "seal" refers to an item that is situated between two components of the device of the present invention, and may function to provide a more efficient and/or stronger connection between the components. A seal may also function to prevent tampering of the devices described herein. The seal can be made of any material known in the art, including but not limited to, PTFE, nitrile, neoprene, silicone, EDPM rubber, fluorocarbon, etc.

As used herein, "treating" or "treatment" or "therapy" refers to ameliorating, preventing, or improving at least one psychological disorder.

As used herein, "vapor" refers to both a substance in the gaseous state and a suspension of finely divided solid particles or liquid droplets in a gas, including aerosols and mists, which functions to deliver the ayahuasca-like substances of the present invention to an end-using consumer. The term "vaporize" refers to the process to producing vapor, e.g., from a vaporizable formulation.

As used herein, a "vaporizable formulation" refers to a liquid (e.g., an oil) and/or solid (e.g., a wax) solution that may be contained within the chamber of the present invention, and which produces a mist or vapour when heated by a heating element that functions to provide a vaporizable carrier for the ayahuasca-like substances described herein.

Delivery Device Chambers

Figure 2A:
FIG. 2A illustrates an exemplary chamber of the present invention using an adaptable "eGo" threaded connector with a "closed" chamber and a 510 connector.
Figure 2B:
FIG. 2B illustrates an adaptable "eGo" threaded connector with an "open" chamber exposing "eGo" threads.
Figure 3:
FIG. 3 illustrates an exemplary chamber of the present invention having a threaded 510 connector and containing a vaporizable formulation (301) comprising dimethyltryptamine.
Figure 4:
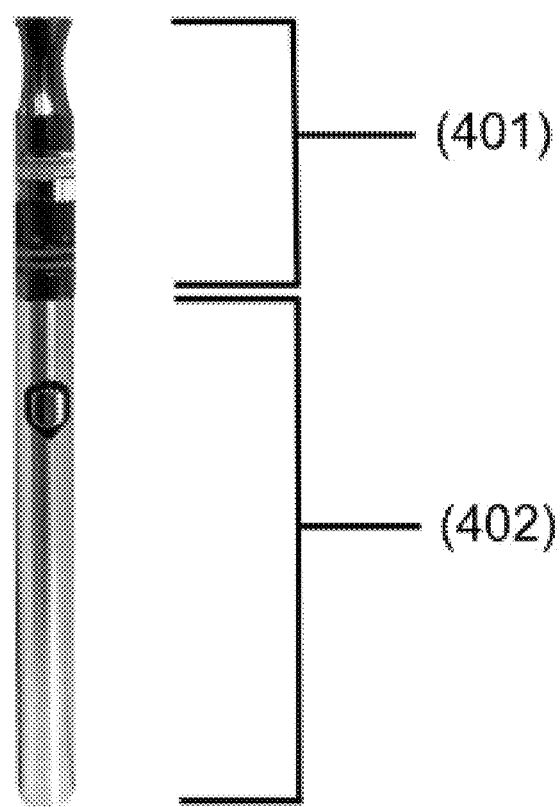
FIG. 4 illustrates an optional embodiment of the present invention wherein a chamber comprising a vaporizable formulation comprising dimethyltryptamine (401) is connected via a 510 threaded connector to a commercially available power unit capable of connecting to 510 threaded connectors (402).

The present invention provides a chamber filled with a vaporizable formulation comprising an ayahuasca-like substance. Non-limiting exemplary chambers are illustrated in FIG. 1 and FIG. 2. An exemplary chamber comprising an ayahuasca-like substance (301) is illustrated in FIG. 3. In some embodiments the chamber is coupled to a power unit capable of providing power to vaporize the formulation (FIG. 4). The heat generated within the chamber via a heating element may vaporize the vaporizable formulation in the chamber adjacent to the heating element present in the chamber. Following vaporization, the vaporizable formulation comprising the ayahuasca-like substance may then mix with air and subsequently be inhaled by the user, which in some embodiments is through a mouthpiece of the chamber that results in an aerosol that is delivered to the user.

A user may desire to have a pre-loaded or manually loaded vaporizable formulation comprising a therapeutic ayahuasca-like substance in the chamber to permit an efficient vaporization of the vaporizable formulation for inhalation and delivery of the substance to the user without having to measure, weigh, touch, or risk spilling the vaporizable formulation to be vaporized and consumed. A pre-loaded chamber further reduces the risk of contact of the vaporizable formulation during many aspects of the supply chain, thus reducing the potential for improper dosing or contamination. Alternatively, a user may desire to have the ability to load the chamber themselves. The chamber may be either refillable or single-use, pre-loaded or loaded prior to use. Numerous delivery device chambers known in the art can be used to practice the present invention, including but not limited to portable or desktop vaporizable cartridges or tanks.

In an embodiment the chamber comprises a bottom portion adapted for coupling to a power unit capable of providing power to vaporize the vaporizable formulation. In an embodiment the chamber is coupled to the power unit capable of providing power to vaporize the vaporizable formulation. Any manner of coupling the power unit to the chamber is sufficient. The chamber may be locked to the power unit. In such embodiments the power unit may be locked as a single use device, or maybe locked to a reusable chamber. In some embodiments the power unit may be releasable from the chamber, which a user may find useful for recharging the power unit.

In an embodiment a connector (103) is provided to connect the chamber to the power unit to permit a heating element that may be integrated within the chamber to provide heat for vaporization of the vaporizable formulation. Such connections are well known in the art. For example, the connector may include a tenon (or "male" component) to connect the chamber to a mortise (or "female" component) configured within the power unit. In most embodiments the chamber will have the tenon and the power unit will have the mortise.

In an embodiment, the tenon may include threads complementary to the threads of the power unit in a standard connection known in the art as a "510 connection," or a "510 connector," or as having "510 threads," or any colloquial variation thereof. By way of example, a "510 connector" is a connector having a 510 thread as commonly referred to in the art. In preferred embodiments a "510 connector" means the chamber is adapted with a 510 threaded tenon and the power unit has a 510 compatible mortise able to accept a 510 threaded tenon, as is commonly referred to in the art. In another embodiment the threads of the power unit may utilize an "eGo connection," or an "eGo connector," or have "eGo threads."

In other embodiments the chamber may utilize a "401 connection," or a "401 connector," or have "401 threads." In an embodiment the chamber unit may utilize a "601 connection," or a "601 connector," or have "601 threads." In an embodiment the chamber may utilize a "610 connection," or a "610 connector," or have "610 threads." In an embodiment the chamber may utilize a "710 connection," or an "710 connector," or have "710 threads." In an embodiment the chamber may utilize an "808 connection," or an "808 connector," or have "808 threads." In an embodiment the chamber may utilize a "901 connection," or a "901 connector," or have "901 threads." In an embodiment the chamber may utilize a "4081 connection," or a "4081 connector," or have "4081 threads." In an embodiment the chamber may utilize a "CE-4 connection," or a "CE-4 connector," or have "CE-4 threads." In an embodiment the chamber may utilize an "E9 connection," or an "E9 connector," or have "601 threads." In an embodiment the chamber may utilize a "CE-5 connection," or a "CE-5 connector," or have "CE-5 threads." Any other suitable connections for providing an electrical connection to the chamber from the power unit as is known in the art may be used.

In some embodiments the chamber may include more than one, or multiple types of thread connections that are easily adaptable to create numerous permutations of thread types for adaptability between connection types. In an embodiment, both 510 and eGo threads are configured to the same chamber such that a 510 thread connector is adapted to be used with an eGo thread connector to permit connection versatility (FIG. 2). In an embodiment, both 401 and eGo threads are configured to the same chamber such that a 401 thread connector is adapted to be used with an eGo thread connector to permit connection versatility. In an embodiment, both 601 and eGo threads are configured to the same chamber such that a 601 thread connector is adapted to be used with an eGo thread connector to permit connection versatility. In an embodiment, both 610 and eGo threads are configured to the same chamber such that a 610 thread connector is adapted to be used with an eGo thread connector to permit connection versatility. In an embodiment, both 710 and eGo threads are configured to the same chamber such that a 710 thread connector is adapted to be used with an eGo thread connector to permit connection versatility. In an embodiment, both 808 and eGo threads are configured to the same chamber such that an 808 thread connector is adapted to be used with an eGo thread connector to permit connection versatility. In an embodiment, both 901 and eGo threads are configured to the same chamber such that a 901 thread connector is adapted to be used with an eGo thread connector to permit connection versatility.

In some embodiments the chamber comprises a top portion adapted for coupling to a mouthpiece (101) wherein the top portion of the chamber comprises at least one air aperture adapted to permit the flow of air, liquid, or vapor between the top portion of the chamber and the mouthpiece.

The mouthpiece may be many different sizes and shapes, for example, flat, round, oval, square, rectangular, etc. The mouthpiece may be made of any suitable material, including but not limited to, plastic, glass, ceramic, silicon, stainless steel, or wood. In some embodiments the mouthpiece is coupled to the top portion of the chamber and the mouthpiece has a bottom portion comprising an aperture to permit liquids, solids, vapor, or air to flow from the chamber to the mouthpiece. In some embodiments the mouthpiece has a central open bore to permit liquids, solids, vapor, or air to flow through the mouthpiece; and in some embodiments, the mouthpiece has a top aperture to permit liquids, solids, vapor, or air to exit the mouthpiece in order to be inhaled or utilized by a user.

In an embodiment, the chamber includes a seal that is situated between the bottom opening of the mouthpiece and the top portion of the chamber. The seal can be made of any material known in the art, including but not limited to, PTFE, nitrile, neoprene, silicone, EDPM rubber, fluorocarbon, etc. In an embodiment, the mouthpiece is releasably coupled to the top portion of the chamber. Releasably coupled mouthpieces may be useful for refilling and multiple uses of chambers. Any mechanism known in the art can be used to permit the mouthpiece to be releasable from the topic portion of the chamber, including but not limited to tenon and mortises with or without threads. In an embodiment, the mouthpiece is lockably coupled to the top portion of the chamber. Locked configurations are useful to prevent tampering with the chamber and/or vaporizable formulation.

The chamber may include a heating element to provide heat that will vaporize the vaporizable formulation comprising the ayahuasca-like substance present within the chamber. During use, power may be supplied to a heating element positioned within the chamber through the application of voltage generated by the power unit to the threads of the tenon, as described herein, which is then transferred to the heating element positioned within the chamber.

Many different types of heating elements may be used. The heating element may include a coil and wick, many of which are well known in the art. Exemplary coils are the kanthal ceramic coil, kanthal (FeCrAl) derivatives, nichrome, aluminum, stainless steel, nickel, and titanium. Many different grades of stainless steel wire may be used. The most popular gauges for the wire are 32, 30, 28, 26, 24, and 22. The type of wicking material can vary and preferably includes the organic cotton for the use with botanical extracts, but in some cases, Japanese cotton pads, ekowool, silica, and rayon fiber may be used. The heating element may also be wickless, as is sometimes used in the art.

The chamber of the present invention will be hollow to some respects such that the vaporizable formulation may be held within the chamber (102). The chamber thus may further include a wall that provides a structural element that further defines an internal volume for containing the vaporizable formulation. The chamber wall can be transparent to permit a user to visualize the amount of vaporizable formulation present within the chamber. An exemplary embodiment of a chamber having a transparent chamber wall permitting visualization of vaporizable formulation is shown in FIG. 3 and FIG. 4. A transparent chamber wall can be glass or plastic. The chamber wall may also include materials that are opaque, or non-light transmitting. For example the chamber may prevent light from entering into the internal volume. As a result, while stored within the chamber, the vaporizable formulation may be free from exposure to light, thus, reducing degradative effects that may arise due to the light.

The chamber may include a lid may provide a seal for the chamber so that the vaporizable formulation located within the internal volume is isolated from the external environment and, for example, is kept from degrading. The sealed chamber may further provide quality control for the vaporizable formulation, which may be pre-processed and packaged therein, providing consistency and reliability of its contents. The chamber may also provide an appropriate environment (e.g., dark, low in relative humidity, inert, etc.) to provide the vaporizable formulation with a relatively long shelf-life. Thus, the chamber in accordance with the present disclosure may be kept for long periods of time without suffering degradation of the contents therein and, for example, may be easily transported, sold in stores, used in vending dispense machines, etc.

The chamber may further include readable information, for example, given by clear labelling (e.g., markings) on an exterior surface of the chamber, for providing to a user and/or system information regarding its contents. Such information may ultimately be relevant in subjecting the vaporizable formulation to conditions that predictably result in a preferred vapor, with consistency in effects/experience, quality, taste and/or smell.

The chamber may include a filtering mechanism, such as one or more filters located on either side of the vaporizable formulation, for removing undesirable particulates and/or other contaminants from the vaporizable formulation as it travels away from the internal volume of the chamber.

The chamber may also include a support member to hold the vaporizable formulation within the internal volume of the chamber during vaporization. The support member may suspend or otherwise distribute the vaporizable formulation within the internal volume during exposure to vaporization heat.

It can be appreciated that a number of different types, shapes, sizes of chambers may be possible, for use with a variety of different power units. The chamber of the present invention can be commonly used cartridges having 0.25 ml, 0.50 ml, and 1.0 ml capacities. The chamber of the present invention can be commonly used tanks or sub ohm tanks having non-limiting capacities of 2 ml, 3 ml, 4 ml, 5 ml or greater.

The chamber wall may have a cylindrical shape, a conical shape, a domed shape and/or a tapered construction. In some cases, the particular shape or structure of the chamber may allow it to be suitably placed within a complementary receptacle of a power unit. The shape/structure of the chamber may also provide for a suitable funneling or Venturi effect of the vapor. For instance, an upper end of the chamber may be tapered or dome-shaped such that vapor arising from the chamber is funneled upward toward an opening and into a collection area (e.g., bag, canister, mouthpiece, flow tube, etc.) where the vapor may be stored or otherwise contained for subsequent consumption.

In some embodiments it may be preferable to provide a chamber that holds a number of different vaporizable formulations (e.g., having varying types/blends) inside. And it may be further preferable for these different vaporizable formulations to be kept separate during storage. The chamber can include a dividing wall that partitions the internal volume of the chamber into multiple sub-chambers or compartments. For example, the chamber and the power unit may be arranged such that only one of the different types/blends of vaporizable formulations comprising an ayahuasca-like substance is vaporized at a time. Or, vaporization may occur in succession, where the process of vaporization/extraction occurs for each of the vaporizable formulations comprising an ayahuasca-like substance during offset time periods. In some cases, it may be preferable for the power unit to have multiple lines through which separate parts of the chamber may be subject to vaporization and extraction. That is, different compartments of the chamber may be individually heated and subject to separate air flows, allowing for more customized vapors to be produced, with blending of the ingredients at different times during the vaporization process. In various embodiments, the chamber may include materials that exhibit high temperature tolerance that are able to withstand relatively high heat temperatures.

The chamber further provides dose-specific and consistent amounts of vaporizable formulations and ayahuasca-like substance concentrations for ease of use applications. Doses can be measured and pre-packaged, and heated precisely to a temperature that produces a therapeutically-active concentration of ayahuasca-like substances. Such dose-specific efficiency increases the present invention's commercial and medicinal value. The chamber may also be configured to permit control over the airflow to the heating element or through the mouthpiece so that the user may adjust the amount of vapor being released.

The chamber may also be configured to have inlet holes to regulate flow of the vaporizable formulation from the chamber to the external environment for inhalation, which may be desirable for vaporizable formulations having different viscosities. Commonly used sizes in the art, for example, may inlet holes can have non-limiting diameters of less than or equal to 1.2 mm, 1.4 mm, 1.6 mm, 1.8 mm, 2.0 mm, or greater.

The internal volume of the chamber within which the vaporizable formulation is stored may be substantially removed of oxidizing or otherwise deleterious substances. For instance, prolonged exposure of the vaporizable formulation to oxygen may have negative consequences and may reduce the overall quality of the vapor produced therefrom. For example, exposure to oxygen may result in the occurrence of undesirable oxidation or other reaction(s), which may remove a number of desirable qualities from the vaporizable formulation comprising the ayahuasca-like substance. To remove oxygen, an inert air (e.g., nitrogen gas, noble gas, etc.) may be flushed through the chamber. Accordingly, when suitably packaged, the vaporizable formulation may be stored in a relatively inert environment substantially devoid of oxygen. When appropriately packaged, the internal volume of the chamber may also be maintained at a suitable level of relative humidity, as measured according to methods known in the art. It may be preferable for the vaporizable formulation to be stored within a relatively dry environment to reduce opportunities for degradation.

The chamber may further include a filtering system. For instance, the filter(s) may be constructed to trap unwanted particles that may arise during vaporization of the vaporizable formulation comprising the ayahuasca-like substance. However, in some instances, it may be preferable for the filter(s) to be constructed such that the vaporizable formulation, or derivatives therefrom (e.g., oils, residue, vapor, etc.), does not clog the filter(s). In some embodiments, the filter(s) may include a fine mesh that allows vapor produced from the vaporizable formulation to pass freely therethrough, for example, without an undesirable amount of condensation or accumulation of debris.

Power Units

An optional embodiment of the present invention is a chamber connected to a power unit, as illustrated in FIG. 4. Power units (also sometimes referred to in the art as batteries) are devices used to provide power to vaporize a vaporizable formulation comprising an ayahuasca-like substance within the chamber of the present invention, for the purpose of inhalation. During use, the application of voltage is generated by a power source within the power unit, which is then passed through to the threads of the chamber. This permits a heating element positioned within the chamber to generate heat in order to vaporize the vaporizable formulation in the chamber adjacent to a heating element present in the chamber.

Numerous types and examples of power units, both portable and "desktop," are well known in the art, any one of which may be sufficient to practice the present invention. The power unit may generate heat using many methods well known in the art, and may be configured to heat the vaporizable formulation through a wide range of incremental heats based on the preferences of the user.

The power unit may be charged by any method well known in the art to provide power to the heating unit, including but not limited to the use of rechargeable batteries. Rechargeable batteries can be recharged using many methods known in the art, for example, via a USB recharging system.

In some embodiments, a power unit may be equipped with a controller that is configured to obtain information regarding the contents of the vaporizable formulation comprising an ayahuasca-like substance based on the readable information. For instance, the power unit may have an information reader, such as a digital code reader (e.g., for barcodes, QR codes, etc.) for reading the readable information on the surface of the chamber and/or user interface, for providing input to the controller of the information about the vaporizable formulation comprising an ayahuasca-like substance. Based on this input, the power unit may process the vaporizable formulation comprising an ayahuasca-like substance within the chamber according to a specific vaporization recipe, to produce a vapor having particularly desirable characteristics. For example, the power unit may flow air through the chamber as well as provide a temperature profile within the chamber for extracting a suitable combination of chemical compounds according to a specified protocol. In some embodiments, this temperature profile may include a number of timed temperature adjustments that occur during the period of vaporization when extraction of the vaporization formulation comprising an ayahuasca-like substance occurs. In some cases, the power unit may provide this temperature profile as part of an automated process of vaporization and extraction, or a user may input such a profile into the power unit. Vapor generated from the vaporizable formulation comprising an ayahuasca-like substance is then passed from the internal volume of the chamber externally, or alternatively, to a bag, canister and/or other collection region, for consumption by a user.

The power unit may include sensors to provide a user with an appropriate notification (e.g., audio/visual/tactile signal(s)) as the production of vapor is ongoing, or completed. In some embodiments, a sensor coupled with the power unit that tracks the progress of vapor production may be employed so as to present the user with a real-time status report of the vapor being generated, or even if the vapor is being generated at all. For example, such a report may be an indicator for how full the chamber is, the particular concentration of one or more ayahuasca-like substances within the vapor, whether the vaporization cycle has been completed, the existence of vapor produced, etc. Hence, at an appropriate time (e.g., when the chamber is full of vapor, when the user wants to stop the cycle, etc.), the chamber may be removed from the power unit and the user may sip and/or breathe the vapor through a suitable mouthpiece.

The power unit may be configured to process the chamber and its contents so as to extract the ayahuasca-like substances as fully as possible therefrom. Accordingly, the power may control the overall dosage of vapor and extraction by varying a number of parameters during certain steps such as cycle time, start/stop times, temperature settings, rate of air flow therethrough, relative humidity, amongst others, the combination of which may play a substantial role in producing a desirable amount of substance and flavor.

The power unit may also be configured as a smart machine that learns the preferences of a user. For example, a user may input a number of parameters and/or the power unit may track the particular conditions for vaporizing the contents of the chamber. The user may determine that a certain set of conditions may be especially effective in producing a vapor that achieves a favorable experience. The vaporizer may also track specific combinations of chamber and vaporization conditions that correspond to favorable user experiences, and may communicate such combinations to the user for later use, as suitably desired.

In an embodiment a power unit may be made available in combination with the chamber, and may be releasably coupled to the chamber. In an embodiment a power unit may be made available in combination with the chamber, and may be lockabley coupled to the chamber. In embodiments where the power unit is lockabley coupled to the chamber, the purpose may be for a "all in one" single use application. However, power units may be lockably coupled to a refillable chamber as described herein, if desired by a consumer.

Vaporizable Formulations

Included in the present invention are vaporizable formulations, sometimes referred to in the art as "vape juice," or "e-liquid," or "e-juice," and which refers to a liquid (e.g., an oil) and/or solid (e.g., a wax) solution that may be contained within the chamber of the present invention, and which produces a mist or vapour when heated by a heating element that functions to provide a vaporizable carrier for the ayahuasca-like substances described herein.

The vapor may include a mist, aerosol and/or nebulized composition that includes fine solid and/or liquid particles suspended in a gas or, in some cases, the vapor may be substantially formed as a gas. The vapor may also include a gaseous substance having small droplets of oil, water and/or other chemical compounds suspended therein. In some cases, a vapor includes liquid (e.g., water, oil, etc.) particles mixed with hot ambient air, which is cooled down so as to condense into a fine cloud of visible airborne droplets. Accordingly, the vaporizable formulation may be breathed or otherwise administered as medication and/or as therapy in a vaporized form.

In an embodiment, the vaporizable formulation is a mix of propylene glycol (PG) and vegetable glycerin (VG). The vaporizable formulation of the present invention may contain any ratio of PG/VG based on user preference, for example, between 0:100 PG:VG and 10:90 PG:VG, between 10:90 PG:VG and 20:80 PG:VG, between 20:80 PG:VG and 30:70 PG:VG, between 30:70 PG:VG and 40:60 PG:VG, between 40:60 PG:VG and 50:50 PG:VG, between 50:50 PG:VG and 60:40 PG:VG, between 60:40 PG:VG and 70:30 PG:VG, between 70:30 PG:VG and 80:20 PG:VG, between 80:20 PG:VG and 90:10 PG:VG, or between 90:10 PG:VG and 100:0 PG:VG.

The vaporizable formulation may also include water, terpene, and/or polyethylene glycol (PEG) as the vaporizable formulation, and in combination with any ratio of PG and VG. The PEG can be of any molecular weight, including but not limited to, PEG200 and PEG 400. The vaporizable formulation of the present invention may contain any ratio of PEG/VG based on user preference, for example, between 0:100 PEG:VG and 10:90 PEG:VG, between 10:90 PEG:VG and 20:80 PEG:VG, between 20:80 PEG:VG and 30:70 PEG:VG, between 30:70 PEG:VG and 40:60 PEG:VG, between 40:60 PEG:VG and 50:50 PEG:VG, between 50:50 PEG:VG and 60:40 PEG:VG, between 60:40 PEG:VG and 70:30 PEG:VG, between 70:30 PEG:VG and 80:20 PEG:VG, between 80:20 PEG:VG and 90:10 PEG:VG, or between 90:10 PEG:VG and 100:0 PEG:VG. The vaporizable formulation of the present invention may contain any ratio of PG/PEG based on user preference, for example, between 0:100 PG:PEG and 10:90 PG:PEG, between 10:90 PG:PEG and 20:80 PG:PEG, between 20:80 PG:PEG and 30:70 PG:PEG, between 30:70 PG:PEG and 40:60 PG:PEG, between 40:60 PG:PEG and 50:50 PG:PEG, between 50:50 PG:PEG and 60:40 PG:PEG, between 60:40 PG:PEG and 70:30 PG:PEG between 70:30 PG:PEG and 80:20 PG:PEG, between 80:20 PG:PEG and 90:10 PG:PEG, or between 90:10 PG:PEG and 100:0 PG:PEG.

The present invention should not be limited by variability in the purity, kinds and concentrations of chemicals used in liquids, and significant variability between labeled content and concentration and actual content and concentration.

A skilled artisan will be familiar with a substantial range of vaporizable formulations that can be used with the present invention, and any substance that is vaporizable and capable of acting as a carrier for the ayahuasca-like substance will suffice. Numerous naturally extracted e-liquids may be used as the vaporizable formulation for the present invention, for example, the e-liquids described in United States Patent Application No. 20160309775.

Traditional ayahuasca preparations include monoamine oxidase inhibitors (MAOIs). Thus the vaporizable formulation of the present invention can further include one or more MAOIs, which are well known in the art, and can include, but not be limited to, Clorgyline, Minaprine, and the reversible MAO-A inhibitors Befloxatone, Brofaromine, Cimoxatone, Harmaline, Moclobemide, Pirlindole and Toloxatone. Examples of MAO-B inhibitors include, but are not limited to, Rasagiline, Selegiline and Pargyline. Examples of unselective MAO-A and MAO-B inhibitors include, but are not limited to, Iproclozide (Sursum), Iproniazid (Marsilid, Iprozid, Ipronid, Rivivol, Propilniazida), Isocarboxazid (Marplan), Mebanazine (Actomol), Metfendrazine (H.M.-11), Nialamide (Niamid), Phenelzine (Nardil), Pheniprazine (Caton), Phenoxypropazine (Drazine), Pivalylbenzhydrazine (Tersavid, Neomarsilid), Safrazine (Safra) and Tranylcypromine (Parnate). See, for example, Remington: The Science and Practice of Pharmacy, 21st Edition, (2005, Lippincott Williams & Wilkins), pages 1517-1523, and Physicians' Desk Reference, Edition 60 (2006, Thomson PDR) page 1499 (each of which is incorporated herein by reference).

The vaporizable formulation may further include additional components so that users may choose to modify or boost their flavor or concentration of the ayahuasca-like substance with various offerings, including flavorings (non-limiting examples known in art such terpenes, flavonoids, mint, ginger, cinnamon, vanilla, pepper jack cheese, chocolate and peanut butter, Pennsylvania fruit cake, chamomile, ginko, Izzy treats, mango, etc.), and other additives or ingredients, as suitably desired.

Other compositions may also be included in the vaporizable formulation to complement the ayahuasca-like substance. For example, the vaporizable formulation may also include flavonoids, terpenoids, amino acids, proteins, sugars, enzymes, fatty acids, esters and/or other compounds, including but not limited to cannabinoid extracts from *cannabis*, THC, THCv, ketorolac, morphine, testosterone, ibuprofen, codeine, nicotine, Vitamin A, Vitamin E acetate, Vitamin E, nitroglycerin, pilocarpine, mescaline, testosterone enanthate, menthol, phencaramide, methsuximide, eptastigmine, promethazine, procaine, retinol, lidocaine, trimeprazine, isosorbide dinitrate, timolol, methyprylon, etamiphyllin, propoxyphene, salmetrol, vitamin E succinate, methadone, oxprenolol, isoproterenol bitartrate, etaqualone, Vitamin D3, ethambutol, ritodrine, omoconazole, lomustine, ketamine, ketoprofen, cilazaprol, propranolol, sufentanil, metaproterenol, pentoxapylline, captopril, loxapine, cyproheptidine, carvediol, trihexylphenadine, alprostadil, melatonin, testosterone proprionate, valproic acid, acebutolol, terbutaline, diazepam, topiramate, pentobarbital, alfentanil HCl, papaverine, nicergoline, fluconazole, zafirlukast, testosterone acetate, droperidol, atenolol, metoclopramide, enalapril, albuterol, ketotifen, isoproterenol, amiodarone HCl, zileuton, midazolam, oxycodone, cilostazol, propofol, nabilone, gabapentin, famotidine, lorezepam, naltrexone, acetaminophen, sumatriptan, bitolterol, nifedipine, phenobarbital, phentolamine, 13-cis retinoic acid, droprenilamine HCl, amlodipine, caffeine, zopiclone, tramadol HCl, pirbuterol, naloxone, meperidine HCl, trimethobenzamide, nalmefene, scopolamine, sildenafil, carbamazepine, procaterol HCl, methysergide, glutathione, olanzapine, zolpidem, levorphanol, buspirone, and mixtures thereof.

The vaporizable formulations of the present invention need not be limited to oils, and may also include other liquids or waxes. In some embodiments the vaporizable formulation can be adapted for dry vaporization, or be adapted for wax vaporization. In some embodiments, the vaporizable formulation can be adapted for a combination of one or more oil, dry, or wax vaporizable formulations The present invention may be practiced using a variety of different embodiments, including pre-filled chambers that are single use, or refillable. In another embodiment, a vaporizable substance is provided comprising an ayahuasca-like substance, which can be made available separately from the other components of the devices described herein, such that an end-using consumer can refill their chamber after the initial chamber prefilled with the vaporizable formulation is depleted. In another embodiment, the vaporizable formulation can be made available separate from the chamber such that a consumer can adapt their own chamber to be configured with the vaporizable formulations.

Ayahuasca-Like Substances

In some embodiments the vaporizable formulations as described herein comprise an ayahuasca-like substance that is provided for medicinal, therapeutic and/or recreational purposes. The substance may include matter derived from a plant, used for consumption, such as for medicinal, therapeutic, aromatic and/or culinary purposes.

In an embodiment, ayahuasca-like substance may be dimethyltryptamine (also referred to as N,N-dimethyltryptamine, or DMT):

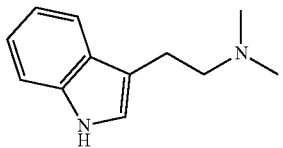

The ayahuasca-like substance does not need to be limited to substances commonly found in ayahuasca, and can include other substances as well, by way of example and not meant to be limiting, 5-methoxy-N,N-dimethyltryptamine or 2-5-dimethoxy-4-bromophenethylamine. The ayahuasca-like substance can further include isotopomer and isotopologue variations, for example, a DMT isotopomer or isotopologue comprising deuterium or tritium.

Ayahuasca-like substances are often combined with MAOIs, many of which are included in the vaporizable formulation and described elsewhere herein.

The ayahuasca-like substances of the present invention can be synthesized by a variety of methods known to one of skill in the art (see Comprehensive Organic Transformations Richard C. Larock, 1989) or by an appropriate combination of generally well known synthetic methods. Dimethyltryptamine can be synthesized through several possible pathways from different starting materials. A common method skilled artisans use to synthesize dimethyltryptamine is through reaction of indole with oxalyl chloride followed by reaction with dimethylamine and reduction of the carbonyl functionalities with lithium aluminum hydride. Another method commonly known for the synthesis of dimethyltryptamine is through the n,n-dimethylation of tryptamine using formaldehyde followed by reduction with sodium cyanoborohydride or sodium triacetoxyborohydride. Techniques useful in synthesizing the ayahuasca-like substances of the present invention are both readily apparent and accessible to those of skill in the relevant art.

A skilled artisan will appreciate that other methods of making the ayahuasca-like substances of the present invention are possible, including but not limited to the extraction and/or purification from plants and other natural substances. Dimethyltryptamine is found in many naturally occurring substances, including but not limited to, *Mimosa hostilis, Mimosa tenuiflora, Phalaris arundinacea, Phalaris aquatica, Diplopterys cabrerana, Psychotria viridis, Acacia confusa, Anadenanthera peregrina*, and *Anadenanthera colubrina*. Methods of extracting dimethyltryptamine from natural substances are well known in the art, and may include the non-limiting methods incorporating the use of a non-polar hydrocarbon solvent and a subsequent alkaline purification, or an acid-base extraction.

It should be stressed that dimethyltryptamine can be synthesized or extracted using a variety of different well known methodologies, and need not be limited to any specific synthesis and/or extraction method specifically described herein.

Most ayahuasca-like substances are readily available and need not be synthesized or extracted. For example, dimethyltryptamine, which was first synthesized in 1931, is readily available in decriminalized jurisdictions.

The present invention is not intended to be limited to any specific weight per volume concentration of the ayahuasca-like substance dissolved in the vaporizable formulation, and may comprise a weight per volume content of greater than 0.1 w/v %, greater than 1.0 w/v %, greater than 10.0 w/v %, greater than 20.0 w/v %, greater than 30.0 w/v %, greater than 40.0 w/v %, greater than 50.0 w/v %, greater than 60.0 w/v %, greater than 70.0 w/v %, greater than 80.0 w/v %, greater than 90.0 w/v %, greater than 100.0 w/v %, greater than 125.0 w/v %, greater than 150.0 w/v %, greater than 200.0 w/v %; or less than 200.0 w/v %, less than 150.0 w/v %, less than 125.0 w/v %, less than 100.0 w/v %, less than 90.0 w/v %, less than 80.0 w/v %, less than 70.0 w/v %, less than 60.0 w/v %, less than 50.0 w/v %, less than 40.0 w/v %, less than 30.0 w/v %, less than 20.0 w/v %, less than 10.0 w/v %, less than 1.0 w/v %, or less than 0.1 w/v %. Combinations of the above-noted ranges, or values outside of these ranges, may be possible for the ayahuasca-like substance content levels of the vaporizable formulation based on user preference or for medicinal optimization.

Methods of Use

In some embodiments, the present invention describes methods of using the chambers described herein. Such methods are particularly useful for refillable chambers or for end users who wish to load chambers with the vaporizable formulations comprising the anahuasca-like substances themselves.

In an embodiment, a method for delivering an ayahuasca-like substance as described herein is provided wherein the method of use comprises heating a vaporizable formulation comprising the ayahuasca-like substance as described herein to vaporize at least a portion of the vaporizable formulation.

In some embodiments the vaporizable formulation of the methods of use of the present invention may be housed in a chamber comprising a top portion adapted for coupling to a mouthpiece and wherein the top portion comprises at least one air aperture adapted to permit flow of air, liquid, or vapor between the chamber and the mouthpiece as described herein. In some embodiments the mouthpiece used by the method of use may comprise a top aperture, a central open bore, and a bottom portion comprising an aperture and coupled to the chamber as described herein. In some embodiments the chamber used by the method of use may comprise at least one seal situated between the bottom opening of the mouthpiece and the top portion of the chamber as described herein. In some embodiments the mouthpiece used in the method of use may be releasably coupled to the top portion of the chamber as described herein. In some embodiments, the mouthpiece used in the method of use may be lockably coupled to the top portion of the chamber as described herein. In some embodiments the chamber used in the method of use may comprise a bottom portion adapted for coupling to a power unit capable of providing power to vaporize the vaporizable formulation as described herein. In some embodiments the chamber used in the method of use may be transparent to permit visualization of levels of the vaporizable formulation.

In some embodiments the chamber used by the methods of use of the present invention may be coupled to the power unit capable of providing power to vaporize the vaporizable formulation as described herein; in some embodiments the chamber used by the method is releasably coupled to the power unit as described herein. In some embodiments the chamber used by the methods of use of the present invention may be lockably coupled to the power unit as described herein; in some embodiments the chamber used by the method may comprise one or more of a 401, 510, 601, 610, 710, 808, 901, 4081, CE-4, CE-5, E9, or eGo connector to couple the chamber to the power unit as described herein; in an embodiment the chamber used by the methods of use of the present invention comprises a 510 connector as described herein.

In some embodiments the chamber used in the methods of use of the present invention is refillable as described herein, although it should be noted that the methods of the present invention should not be limited to refillable chambers, and users may choose to practice the methods of use of the present invention using single use applications.

In some embodiments the ayahuasca-like substance used in the methods of use of the present invention may comprise one or more of dimethyltryptamine, a monoamine oxidase inhibitor, 5-methoxy-N,N-dimethyltryptamine, or 2-5-dimethoxy-4-bromophenethylamine as described herein. In an embodiment the ayahuasca-like substance used by the methods of use of the present invention comprises dimethyltryptamine as described herein. In an embodiment, the ayahuasca-like substance of the methods of use of the present invention comprises an isotopomer or isotopologue of one or more of dimethyltryptamine, a monoamine oxidase inhibitor, 5-methoxy-N,N-dimethyltryptamine, or 2-5-dimethoxy-4-bromophenethylamine. In an embodiment, the ayahuasca-like substance of the methods of use of the present invention is dimethyltryptamine comprising deuterium.

In some embodiments the vaporizable formulation used in the methods of the present invention may comprise one or more of propylene glycol (PG), vegetable glycerin (VG), or polyethylene glycol (PEG), or any other compound as described herein.

Methods of Treatment

Therapeutic benefits of psychedelic drugs, such as dimethyltryptamine, lysergic acid diethylamide and psilocybin, are being actively researched in humans. Studies in healthy volunteers have shown long-term increases in trait optimism (Carhart-Harris et al., Psychological Medicine 2016, 46:1379-1390), well-being (Id. and Griffiths et al., Psychopharmacology 2011, 218:649-665), and openness (Carhart-Harris et al., Psychological Medicine 2016, 46:1379-1390; MacLean et al., Journal of Psychopharmacology 2011, 25:1453-1461), neurodegenerative disorders (Morales-Garcia et al, Translational Psychiatry, 10:331 (2020)), and studies in patients have found long-term improvements in obsessive compulsive disorder (Moreno et al., Journal of Clinical Psychiatry 2006, 67:1735-1740), nicotine addiction (Garcia-Romeu et al., Current Drug Abuse Reviews 2014, 7:157-164), alcoholism (Krebs and Johansen, Psychopharmacology 2012, 26.7:994-1002; Bogenschutz et al., Journal of Psychopharmacology 2015, 29.3:289-299), narcotic addiction (Savage and McCabe, Psychiatry 1973, 28.6:808-814), depression and anxiety related to diagnosis of a life-threatening or terminal illness (Grob et al., Archives of General Psychiatry 2011, 68:71-78; Griffiths et al., Journal of Psychopharmacology 2016, 30(12):1181-1197; Ross et al., Journal of Psychopharmacology 2016, 30(12):1165-1180), and depression (Carhart-Harris et al., The Lancet Psychiatry 2016; Sanches et al., Journal of Clinical Psychopharmacology 2016, 36:77-81) after treatment with psychedelics. Other psychological disorders can include, but are not limited to general anxiety, major depressive disorder, dysthymic disorder, bipolar disorder, panic attacks, schizophrenia, attention deficit disorder, attention deficit hyperactivity disorder, impulse disorders, delusional disorders, cluster headaches, migraines, personality disorders, gambling disorders, eating disorder, body dysmorphic disorder, and other psychological disorders described in the "Diagnostic and Statistical Manual, Version IV." These long-term positive effects can endure for several months, if not years, even after the compound has been metabolized and has been excreted from the body.

In some embodiments, the present invention includes methods of treating a psychological disorder comprising administering to a patient an effective amount of an ayahuasca-like substance, wherein the method comprises heating a vaporizable formulation comprising the ayahuasca-like substance to vaporize at least a portion of the vaporizable formulation.

In some embodiments the vaporizable formulation of the methods of treatment of the present invention may be housed in a chamber comprising a top portion adapted for coupling to a mouthpiece and wherein the top portion comprises at least one air aperture adapted to permit flow of air, liquid, or vapor between the chamber and the mouthpiece as described herein. In some embodiments the mouthpiece used by the methods of treatment may comprise a top aperture, a central open bore, and a bottom portion comprising an aperture that is coupled to the chamber as described herein. In some embodiments the chamber used by the methods of treatment may comprise at least one seal situated between the bottom opening of the mouthpiece and the top portion of the chamber as described herein. In some embodiments the mouthpiece used in the methods of treatment may be releasably coupled to the top portion of the chamber as described herein. In some embodiments, the mouthpiece used in the methods of treatment may be lockably coupled to the top portion of the chamber as described herein. In some embodiments the chamber used in the methods of treatment may comprise a bottom portion adapted for coupling to a power unit capable of providing power to vaporize the vaporizable formulation as described herein. In some embodiments the chamber used in the methods of treatment may be transparent to permit visualization of levels of the vaporizable formulation.

In some embodiments the chamber used by the methods of treatment of the present invention may be coupled to the power unit capable of providing power to vaporize the vaporizable formulation as described herein. In some embodiments the chamber used by the methods of treatment is releasably coupled to the power unit as described herein. In some embodiments the chamber used by the methods of treatment of the present invention may be lockably coupled to the power unit as described herein. In some embodiments the chamber used by the methods of treatment may comprise one or more of a 401, 510, 601, 610, 710, 808, 901, 4081, CE-4, CE-5, E9, or eGo connector to couple the chamber to the power unit as described herein. In an embodiment the chamber used by the methods of treatment of the present invention comprises a 510 connector as described herein.

In some embodiments the chamber used in the methods of treatment of the present invention is refillable as described herein, although it should be noted that the methods of treatment of the present invention should not be limited to refillable chambers, and users may choose to practice the methods of the present invention using single use applications.

In some embodiments the ayahuasca-like substance used in the methods of treatment of the present invention may comprise one or more of dimethyltryptamine, a monoamine oxidase inhibitor, 5-methoxy-N,N-dimethyltryptamine, or 2-5-dimethoxy-4-bromophenethylamine as described herein. In an embodiment the ayahuasca-like substance used by the methods of treatment of the present invention comprises dimethyltryptamine as described herein. In an embodiment, the ayahuasca-like substance used in the methods of treatment of the present invention comprises an isotopomer or isotopologue of one or more of dimethyltryptamine, a monoamine oxidase inhibitor, 5-methoxy-N,N-dimethyltryptamine, or 2-5-dimethoxy-4-bromophenethylamine. In an embodiment, the ayahuasca-like substance used in the methods of treatment is dimethyltryptamine comprising deuterium.

In some embodiments the vaporizable formulation used in the methods of treatment of the present invention may comprise one or more of propylene glycol (PG), vegetable glycerin (VG), or polyethylene glycol (PEG), or any other compound as described herein.

The methods of treatment as described herein may be administered by an individual qualified to administer the vaporizable formulations of the present invention in accordance with local jurisdictional laws, which may include, but is not limited to, a psychiatrist, psychologist, therapist, shaman, or any other qualified individual.

Kits

In other embodiments the present invention provides components packaged together in the form of a kit for performing any of the methods described herein.

In some embodiments, the kit comprises a chamber comprising at least one vaporizable formulation wherein the vaporizable formulation comprises an ayahuasca-like substance. In some embodiments, the chamber that is part of the kit comprises a mouthpiece coupled to a top portion of the chamber. In some embodiments the mouthpiece comprises a top aperture, a central open bore, a bottom portion comprising an aperture, and wherein the bottom portion of the mouthpiece is coupled to the top portion of the chamber. In some embodiments, the mouthpiece that is part of the kit is releasably coupled to the top portion of the chamber. In some embodiments, the mouthpiece that is part of the kit is lockably coupled to the top portion of the chamber. In some embodiments, the chamber that is part of the kit is coupled to the power unit capable of providing power to vaporize the vaporizable formulation. In some embodiments, the chamber that is part of the kit is releasably coupled to the power unit. In some embodiments, the chamber that is part of the kit is lockably coupled to the power unit. In some embodiments, the chamber that is part of the kit comprises one or more of a 401, 510, 601, 610, 710, 808, 901, 4081, CE-4, CE-5, E9, or eGo connector to couple the chamber to the power unit. In some embodiments, the chamber that is part of the kit comprises a 510 connector. In some embodiments, the chamber that is part of the kit is transparent to permit visualization of levels of the vaporizable formulation. In some embodiments, the chamber that is part of the kit is refillable. In some embodiments, the ayahuasca-like substance that is part of the kit comprises one or more of dimethyltryptamine, a monoamine oxidase inhibitor, 5-methoxy-N,N-dimethyltryptamine, or 2-5-dimethoxy-4-bromophenethylamine. In some embodiments, the ayahuasca-like substance that is part of the kit comprises dimethyltryptamine. In an embodiment, the ayahuasca-like substance that is part of the kit comprises an isotopomer or isotopologue of one or more of dimethyltryptamine, a monoamine oxidase inhibitor, 5-methoxy-N,N-dimethyltryptamine, or 2-5-dimethoxy-4-bromophenethylamine. In an embodiment, the ayahuasca-like substance that is part of the kit is dimethyltryptamine comprising deuterium. In some embodiments, the vaporizable formulation that is part of the kit comprises one or more of propylene glycol (PG), vegetable glycerin (VG), or polyethylene glycol (PEG).

EXAMPLE

Aspects of the present teachings can be further understood in light of the following example, which should not be construed as limiting the scope of the present teachings in any way.

The following example was performed in a jurisdiction where each substance described has been decriminalized.

Step 1: Dimethyltryptamine

Pure dimethyltryptamine was acquired through readily available channels. Melting point analyses were taken from two samples to confirm the chemical makeup. The two samples each melted at approximately 46 degrees celsius, confirming that the chemical makeup was dimethyltryptamine.

Step 2: Formulating a Vaporizable Formulation

The dimethyltryptamine (i.e., the ayahuasca-like substance) derived from Step 1 was mixed into a formulation comprising propylene glycol (PG) and vegetable glycerin (VG) to formulate a vaporizable formulation comprising the ayahuasca-like substance. The dimethyltryptamine (i.e., the ayahuasca-like substance) derived from Step 1 was also mixed into a formulation comprising polyethylene glycol (PEG) and vegetable glycerin (VG) to formulate a vaporizable formulation comprising the ayahuasca-like substance. Finally, the dimethyltryptamine (i.e., the ayahuasca-like substance) derived from Step 1 was mixed into a formulation comprising propylene glycol (PG) and polyethylene glycol (PEG) to formulate a vaporizable formulation comprising the ayahuasca-like substance.

Dimethyltryptamine was mixed at different concentrations varying from 250 mg/ml to 1 g/ml. Optional formulation ratios are described in Table 1.

TABLE 1

| PG:VG | 0:100 | PEG:VG | 0:100 | PG:PEG | 0:100 |
|---|---|---|---|---|---|
| PG:VG | 10:90 | PEG:VG | 10:90 | PG:PEG | 10:90 |
| PG:VG | 20:80 | PEG:VG | 20:80 | PG:PEG | 20:80 |
| PG:VG | 30:70 | PEG:VG | 30:70 | PG:PEG | 30:70 |
| PG:VG | 40:60 | PEG:VG | 40:60 | PG:PEG | 40:60 |
| PG:VG | 50:50 | PEG:VG | 50:50 | PG:PEG | 50:50 |
| PG:VG | 60:40 | PEG:VG | 60:40 | PG:PEG | 60:40 |
| PG:VG | 70:30 | PEG:VG | 70:30 | PG:PEG | 70:30 |
| PG:VG | 80:20 | PEG:VG | 80:20 | PG:PEG | 80:20 |
| PG:VG | 90:10 | PEG:VG | 90:10 | PG:PEG | 90:10 |
| PG:VG | 100:0 | PEG:VG | 100:0 | PG:PEG | 100:0 |

Step 3: Production of Delivery Device

Step 3 describes an embodiment of the invention wherein a chamber as described herein is combined with an ayahuasca-like substance. The vaporizable formulation of Step 2 comprising the ayahuasca-like substance derived from Step 1 was placed into the hollow portion of a chamber comprising a 510 threaded connector as described herein and illustrated in FIG. 3.

The vaporizable formulation of Step 2 comprising the ayahuasca-like substance derived from Step 1 was also placed into the hollow portion of a chamber comprising an eGo threaded connector as described herein.

Step 4: Attachment to a Power Unit

An optional embodiment of the present invention includes a power unit. The delivery device comprising the chamber of Step 3 comprising the vaporizable formulation of Step 2 comprising the ayahuasca-like substance derived from Step 1 was affixed to a commercially available power unit as shown in FIG. 4.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

What is claimed is:

1. A device for the delivery of a substance comprising: a chamber comprising at least one vaporizable formulation wherein the vaporizable formulation comprises the substance and wherein the substance comprises one or more of dimethyltryptamine, 5-methoxy-N,N-dimethyltryptamine, or 2-5-dimethoxy-4-bromophenethylamine.

2. The device of claim 1 wherein the chamber comprises a top portion adapted for coupling to a mouthpiece wherein the top portion of the chamber comprises at least one aperture adapted to permit flow of air, liquid, solids, or vapor between the top portion of the chamber and the mouthpiece.

3. The device of claim 2 additionally comprising a mouthpiece coupled to the top portion of the chamber wherein the mouthpiece comprises a top aperture, a central open bore, a bottom portion comprising an aperture, and wherein the bottom portion of the mouthpiece is coupled to the top portion of the chamber.

4. The device of claim 3 additionally comprising at least one seal situated between the bottom portion of the mouthpiece comprising an aperture and the top portion of the chamber.

5. The device of claim 2 wherein the mouthpiece is releasably coupled to the top portion of the chamber.

6. The device of claim 2 wherein the mouthpiece is lockably coupled to the top portion of the chamber.

7. The device of claim 1 wherein the chamber comprises a bottom portion adapted for coupling to a power unit capable of providing power to vaporize the vaporizable formulation.

8. The device of claim 7 wherein the chamber is coupled to the power unit capable of providing power to vaporize the vaporizable formulation.

9. The device of claim 8 wherein the chamber is releasably coupled to the power unit.

10. The device of claim 8 wherein the chamber is lockably coupled to the power unit.

11. The device of claim 1 wherein the chamber comprises one or more of a 401, 510, 601, 610, 710, 808, 901, 4081, CE-4, CE-5, E9, or eGo connector.

12. The device of claim 11 wherein the chamber comprises a 510 connector.

13. The device of claim 1 wherein the chamber is transparent to permit visualization of levels of the vaporizable formulation.

14. The device of claim 1 wherein the chamber is refillable.

15. The device of claim 1 wherein the vaporizable formulation further comprises a monoamine oxidase inhibitor.

16. The device of claim 1 wherein the substance is dimethyltryptamine.

17. The device of claim 1 wherein the one or more of dimethyltryptamine, 5-methoxy-N,N-dimethyltryptamine, or 2-5-dimethoxy-4-bromophenethylamine comprises an isotopomer or isotopologue of the one or more of dimethyltryptamine, 5-methoxy-N,N-dimethyltryptamine, or 2-5-dimethoxy-4-bromophenethylamine.

18. The device of claim 17 wherein the isotopomer or isotopologue comprises deuterium.

19. The device of claim 17 wherein the isotopomer or isotopologue of the one or more of dimethyltryptamine, 5-methoxy-N,N-dimethyltryptamine, or 2-5-dimethoxy-4-bromophenethylamine is dimethyltryptamine comprising deuterium.

20. The device of claim 1 wherein the vaporizable formulation comprises one or more of propylene glycol (PG), vegetable glycerin (VG), or polyethylene glycol (PEG).

* * * * *